United States Patent [19]

Shinoki et al.

[11] Patent Number: 6,027,907
[45] Date of Patent: Feb. 22, 2000

[54] METHOD FOR IMMUNOLOGICAL DETERMINATION OF HEMOGLOBIN DERIVATIVE AND TREATING REAGENT FOR USE THEREIN

[75] Inventors: Hiroshi Shinoki; Yoshikazu Amano, both of Saitama, Japan

[73] Assignee: Fuji Photo Film Co., Ltd., Kanagawa, Japan

[21] Appl. No.: 08/767,386

[22] Filed: Dec. 16, 1996

[30] Foreign Application Priority Data

Dec. 14, 1995 [JP] Japan ..................... 7-347289

[51] Int. Cl.[7] ................ G01N 33/53; G01N 33/72; G01N 1/18; G01N 33/539
[52] U.S. Cl. .................. 435/7.9; 436/66; 436/67; 436/177; 436/536; 436/539; 436/815; 530/829; 530/418; 530/424
[58] Field of Search .................. 436/66, 67, 177, 436/536, 539, 815; 530/829, 418, 424; 435/7.9

[56] References Cited

U.S. PATENT DOCUMENTS

| 4,647,654 | 3/1987 | Knowles et al. ............... 530/326 |
| 5,242,842 | 9/1993 | Sundrehagen ................. 436/536 |

FOREIGN PATENT DOCUMENTS

| 185870 | 7/1986 | European Pat. Off. ....... G01N 33/68 |
| 9013818 | 11/1990 | WIPO . |

OTHER PUBLICATIONS

Carvalli et al. Acta Technologiae et Legis Medicamenti 7(2):101–111, 1996 (Abstract).
Damaszewski et al. J. of Colloid and Interface Science 97(1):166–175, 1984 (Abstract).
Baldauf et al. J. of Colloid and Interface Science 85(1):187–197, 1982.
Sigma Chemical Co. 1987, (Price List).
England et al. Precipitation Techniques, In: Methods in Enzymology, vol. 182, Guide to Protein Purification. MP Deutscher (ed), 1990.
Alcohol & Alcoholism Suppl. 1987; pp. 283–287—Y.M. Ostrovsky, et al. Interaction of Ethanol with Blood Protein.

*Primary Examiner*—James C. Housel
*Assistant Examiner*—V. Ryan
*Attorney, Agent, or Firm*—McAulay Nissen Goldberg Kiel & Hand, LLP

[57] ABSTRACT

A hemoglobin derivative-containing sample is treated with a treating reagent containing 2-butanol and then immunologically analyzed to determine the quantity of the hemoglobin derivative. By the treatment with 2-butanol, the immunological determination for the hemoglobin derivative, particularly $HbA_{1c}$, can be attained with high sensitivity by a simple procedure. Since 2-butanol-containing treating reagent does not affect the enzymatic activity, the homogeneous enzyme immunoassay with high sensitivity is realized.

9 Claims, 2 Drawing Sheets

METHOD FOR IMMUNOLOGICAL DETERMINATION OF HEMOGLOBIN DERIVATIVE AND TREATING REAGENT FOR USE THEREIN

BACKGROUND OF THE INVENTION

1. Field of the Invention

The present invention relates to a method for the immunological determination of a hemoglobin derivative, preferably glycated hemoglobin as a hemoglobin derivative, and especially hemoglobin $A_{1c}$. The present invention also relates to a treating reagent to be used in the method of determination mentioned above.

2. Description of the Prior Art

Hemoglobin (Hb) is a respiratory pigment present in erythrocyte, which is largely responsible for oxygen transport. A hemoglobin molecule comprises four polypeptide subunits (respectively two a chain systems and β chain systems), each subunit is formed by association of one globin protein and one heme molecule which is an iron-protoporphyrin complex. Major class of hemoglobin (more than 90%) found in normal adult hemoglobin (HbA: also referred to $HbA_0$ for distinguishing from glycated hemoglobin $HbA_1$ described hereinafter) having $\alpha_2\beta_2$ subunits composition; and trace components such as $HbA_2$ ($\alpha_2\delta_2$) are also found in normal adult.

There are several classes of hemoglobin derivatives in the adult hemoglobin HbAs. The determination of the contents of such hemoglobin derivatives in blood has been gaining in importance under various medical conditions. Among classes of hemoglobin derivatives, glycated hemoglobin proves to be particularly important. This glycated hemoglobin is the generic term for designating the fractions, $HbA_{1a1}$, $HbA_{1a2}$, $HbA_{1b}$, and $HbA_{1c}$, into which HbA is classified by an ion-exchange resin fractionation. It is referred to as $HbA_1$ (also designated as glycosylated hemoglobin). All of these subclasses of the glycated hemoglobins have the same primary structure, which is stabilized by formation of an aldimine (Schiff base) by the amino group of the N terminal valine in the β subunit chain of normal hemoglobin HbA and glucose (or glucose-6-phosphate or fructose) followed by formation of a ketoamine by Amadori rearrangement.

Particularly, the glycated hemoglobin bound with glucose are called as $HbA_{1c}$ (glycosylated hemoglobin, which will be occasionally referred to as hemoglobin $A_{1c}$ hereinafter) and they constitute the greater part of glycated hemoglobins. The content ratio of glycosylated hemoglobin is proportional to the blood glucose level and ranges about 5% in the total hemoglobin Hb of normal human adult. It possibly rise to levels in the range of 8 to 16% in patients of diabetes. The determination of the amount of glycosylated hemoglobin $HbA_{1c}$, therefore, is regarded as a good index for carbohydrate metabolism control. Further, since the ketoamine formed by a non-enzymatic reaction with blood glucose is stable, the glycosylated hemoglobins $HbA_{1c}$ will not decompose during the life of erythrocyte (an average of 120 days). The hemoglobin $A_{1c}$ content in blood, therefore, is construed as recording the blood glucose level in the past one to two months. As a result, the blood glucose level in the last two months or so can be estimated on the basis of the ratio of $HbA_{1c}$ to the total hemoglobin Hb. Thus, the analysis of the hemoglobin $A_{1c}$ in blood is utilized as an index which permits a long-term control of blood glucose level, unlike the short-term index such as blood glucose level which generally rises briefly after a meal.

Various methods have been developed for the analysis for the hemoglobin $A_{1c}$. These methods generally are based on such techniques as electrophoresis, ion-exchange chromatography, and affinity chromatography. These methods invariably do not fit the clinical test which handles numerous samples because they require expensive analytical apparatuses and consume much time for analysis. In this respect, such immunological methods of analysis as the immunoassay which make use of antibodies to hemoglobin $A_{1c}$ are at an advantage in adopting relatively simple procedures and obviating use of much time. Particularly, since specific antibodies to the glycosylated N-terminal residue of $HbA_{1c}$ as specific antibodies to $HbA_{1c}$ are disclosed, for examples, in Unexamined Japanese Patent Publication (KOKAI) Nos. 8743/1989, 172064/1986, and 280571/1986, various immunological methods of determination of $HbA_{1c}$ have been developed (for example, Unexamined Japanese Patent Publication (KOKAI) Nos. 277967/1988 and 46566/1991).

In the field of the immunological determination of $HbA_{1c}$, various treatments are attempted to realize analysis of greater sensitivity by treating the $HbA_{1c}$ in a given sample. Most of the methods adopted for such treatment, however, are not easily applied for an enzyme immunoassay, because the treatments in these method are mainly due to the denaturation process of $HbA_{1c}$ which is a glycoprotein.

Unexamined Japanese Patent Publication No. 155268/1989 (corresponding to U.S. Pat. No. 4,970,171 and EP-A-0315864), for example, discloses a method for determining $HbA_{1c}$ in blood by denaturing hemoglobin in blood with thiocyanate and further converting it to methhemoglobin with an oxidizing agent such as ferricyanide. In this method, hemoglobin is converted or denatured to methhemoglobin having a specific absorption peak at 540 nm, which can be easily detected to facilitate the determination of the total hemoglobin content. The oxidizing agent enhances the efficiency of denaturation of the thiocyanate denaturing agent, thereby the sensitivity of detection of $HbA_{1c}$ in the sample is improved. Although it is desirous that this treatment can be applied to an enzyme immunoassay for analysis of the $HbA_{1c}$, it is difficult to realize such an application, because the labelled enzyme is also affected and inactivated by thiocyanate or the oxidizing agent. Although the enzyme immunoassay may be effectively adopted on the condition that the thiocyanate and the oxidizing agent are removed from the sample after the completion of the treatment, the cumbersome operations are needed for the removal of the agents. Further, since this method uses a cyanide harmful to the environment, the waste liquid problem is raised.

Unexamined Japanese Patent Publication (KOKAI) No. 20452/1989 (corresponding to U.S. Pat. No. 4,800,167 and EP-A-0286915) discloses a method for the determination of total hemoglobin content without the use of a cyanide. This method uses as a denaturing reagent an aqueous solution of polyvinyl pyrrolidone (PVP) which is alkalinized to a level in the range of pH 12 to 14. This denaturing reagent is intended to use the PVP for stabilizing the hemoglobin, which is solubilized with a high alkali, and give rise to a product having the main absorption peak at the wavelength of about 575 nm. The application of this method for the determination of HbAic is conceivable. However, such application it proves unfavorable because the sugar moiety of the $HHbA_{1c}$ molecule is possibly cleavaged or broken in the presence of a strong alkali to change the antigenicity of the $HbA_{1c}$ molecule. The determination of $HbA_{1c}$ by the enzyme immunoassay has also a disadvantage in suffering the enzymatic activity of the labelling enzyme of the antibody to be suppressed since most enzymes have their optimum pH values generally in the neutral range (pH 6 to 8). More importantly, the immunological reaction (antigen-antibody binding reaction) itself is possibly suppressed by a high pH condition. Therefore, this treatment method is not easily applied to the immunoassay.

Unexamined Japanese Patent Publication (KOKAI) No. 11510/1996 (corresponding to DE 4206932A) discloses a method wherein a blood specimen is treated with a hemolysis reagent containing an ionic detergent (surfactant) having a pH value in the range of 5.0 to 9.5. The total hemoglobin content in the hemolyzed sample is analyzed by calorimetric determination. The amount of the hemoglobin $A_{1c}$ in the hemolyzed sample is analyzed by the immunological determination. Examples of ionic detergents to be used in this treatment include anionic detergents such as SDS (sodium dodecyl sulfate) and cationic detergents such as TTAB (tetradecyl trimethyl ammonium bromide). These ionic detergents have been well known as hemolyzing reagents in the art. Since these ionic detergents also have an action of denaturing proteins, they have an adverse effect on the labelled enzyme and inevitably inhibit the enzymatic activity thereof. In the heterogeneous enzyme immunoassay which necessitates B/F separation, the ionic detergent can be removed simultaneously with the B/F separation after the antigen-antibody binding reaction, so that the enzymatic activity may be prevented from the adverse effect by the ionic detergent. When the treatment method with ionic detergents adopts to the homogeneous enzyme immunoassay which does not necessitate the B/F separation, however, the ionic detergent remains in the treated sample solution and inhibit the enzymatic activity of the labelling enzyme, resulting in less sensitivity for practical uses.

Japanese Patent Publication No. 23891/1995 (EP-A-185870, U.S. Pat. No. 4,647,654) discloses a method wherein a protein such as $HbA_{1c}$ is treated and denatured with a chaotropic reagent thereby exposing the epitope of the protein and enhancing the affinity thereof for an antibody. This method is unfit for quick determination because the step of the denaturation consumes a long time ranging from one to several hours at temperatures below 37° C. Since the denaturing reagent used in this method is guanidine hydrochloric acid, urea, SDS, or protease, it is destined to inactivate the enzymatic activity in the same manner as in the prior techniques mentioned above. In the homogeneous enzyme immunoassay, therefore, this method is practically incapable of attaining necessary determination of $HbA_{1c}$.

SUMMARY OF THE INVENTION

The present invention has been accomplished in view of the aforementioned circumstances. The first object of the present invention is to provide a method for the immunological determination of a hemoglobin derivative, which enables an analysis of the hemoglobin derivative with simple and raid operation at a high sensitivity, and particularly fits an enzyme immunoassay including a homogeneous system. The second object of the present invention is to provide a treating reagent for use in the method of determination mentioned above.

The first object of the present invention is achieved by the provision of a method for the immunological determination of a hemoglobin derivative; comprising steps of treating a sample solution containing said hemoglobin derivative with a treating reagent containing 2-butanol, and immunologically analyzing the treated sample solution to determine the quantity of the hemoglobin derivative in the sample solution.

The second object of the present invention is achieved by the provision of a treating reagent for the treatment of a hemoglobin derivative, characterized by containing 2-butanol.

DETAILED DESCRIPTION OF THE INVENTION

Figure 1:
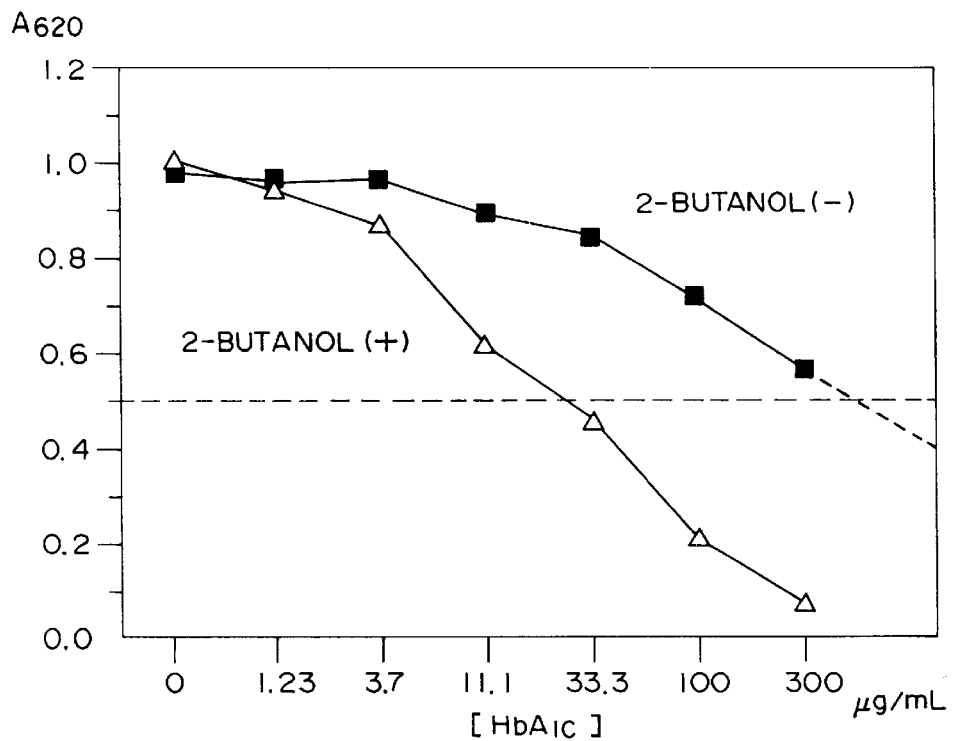
FIG. 1 is a diagram showing the effect of a 2-butanol treatment on the homogeneous enzyme immunoassay. In the diagram, —■— indicates the results obtained of a treating reagent 1 containing no 2-butanol (comparative example) and —Δ— indicates the results obtained of a treating reagent 2 containing a 2-butanol (according to the present invention)

The present inventors have searched for a treating reagent for hemoglobin $A_{1c}$ which enables a homogeneous enzyme immunoassay to be effected with high sensitivity without inhibiting the enzymatic activity of the labelling enzyme. After studying numerous water-soluble organic solvents, the inventors have confirmed that the treatment with 2-butanol alone greatly improves the homogeneous enzyme immunoassay in sensitivity of detection. The inventors have also found that 2-butanol does not inhibit the enzymatic activity of the labelling enzyme.

The inventors have found that the effect of the treatment with an organic solvent in improving the sensitivity of detection is absent from other water-soluble organic solvents such as methanol, ethanol, propanol, isopropanol, 1-butanol, t-butyl alcohol, 1,2-dihydroxy butane, 1,3-dihydroxy butane, 1,4-dihydroxy butane, 2,3-dihydroxy butane, 1,5-dihydroxy pentane, 2,4-dihydroxy pentane, and acetonitrile.

The 2-butanol ($CH_3CH(OH)CH_2CH_3$, sec-BuOH) in the treating reagent according to the present invention is effective for the hemoglobin derivative, at a concentration such that the final concentration at the treatment may be not more than about 20% by weight, preferably about 1.0% to about 5.0% by weight. Within the concentration satisfying this condition, the 2-butanol will exert no adverse effect on the enzymatic activity of labelling enzymes which are in popular use in the enzyme immunoassay. Preferably, treatment with 2-butanol is carried out at a temperature of from about 15° C. to about 40° C., more preferably at a temperature of from about 20° C. to about 38° C. At temperatures in this range, the treatment with 2-butanol is completed within five minutes.

The treating reagent of the invention is used in a water-based solution. The water-based solution of the treating reagent, when necessary, may incorporate therein a hemolysis reagent component. It may also incorporate therein a pH buffer and a stabilizing reagent.

The sample or specimen containing a hemoglobin derivative such as hemoglobin $A_{1c}$ may be a whole blood sample. In this case, the hemolyzing action caused by 2-butanol may be utilized. The blood sample, otherwise, may be preparatorily treated with a known hemolysis reagent to release hemoglobin from erythrocytes and then may be subjected to a denaturing treatment with 2-butanol. A commercially available hemolyzing agent, surfactant, or saponin may be used for this purpose. Alternatively, the hemolysis may be attained by an osmotic shock using a non-isotonic diluent or a high-concentration buffer solution. The erythrocyte membranes, when necessary, may be broken by an ultrasonic disintegration. The hemolysis may be effected by freezing and thawing.

The treating reagent may contain both 2-butanol and a hemolysis reagent to effect the hemolysis treatment and the treatment with 2-butanol at the same time. In the standard clinical test, this method proves convenient because of simplicity of the procedure. When a surfactant is used as a hemolysis reagent, a nonionic surfactant is preferable to be use, since the nonionic surfactant has no suppressing effect to the enzymatic activity of the labelling enzyme. The final concentration of the surfactant at the step of addition thereof to the blood sample (prior to the hemolysis treatment) ranges from 0.01% to 5%, preferably 0.1 to 0.5%.

Preferable examples of the nonionic surfactant to be used advantageously include;
- alkyl phenol polyethylene oxide condensates such as p-(1,1,3,3-tetramethylbutyl) phenoxy polyethoxy ethanol (Triton X-100 containing an average of 9 or 10 oxyethylene units, Triton X-165 containing an average of 16 oxyethylene units, and Triton X-405 containing an average of 40 oxyethylene units, Chemical Abstract Registry No. 9002-93-1);
- alkyl phenol polyglycidol condensates such as p-nonyl phenoxy polyglycidol containing an average of 10 glycidol units;
- polyethylene oxide condensates of higher aliphatic alcohols such as lauryl alcohol polyethylene oxide condensates (such as, for example, Brij 35, Chemical Abstract Registry No. 9002-92-0) and cetyl alcohol polyethylene oxide condensates (such as, for example, Brij 58, Chemical Abstract Registry No. 9004-95-9);
- higher fatty ester condensates of polyethylene glycol such as stearic ester-polyethylene glycol condensates (such as, for example, Myrj 52 and Myrj 59, Chemical Abstract Registry No. 9004-99-3); and
- polyethylene glycol condensates of higher aliphatic sorbitan esters such as polyethylene glycol condensates of sorbitan monolauric esters (such as, for example, Tween 20, Chemical Abstract Registry No. 9005-64-5).

The buffer solution for the 2-butanol treating reagent of the present invention is only required to be incapable of inhibiting the immunological binding reaction and the subsequent enzymatic reaction. Such buffer solution may be selected from a variety of conventional buffer solutions. Preferably, MES, HEPES, or Tris buffer solution is used at a concentration of 10 to 200 mM. The pH value of the treating reagent is in the neutral range or the proximity thereof in which the reagent causes no effect on the immunological binding reaction. Appropriately, this pH value coincides with the optimum pH for the enzymatic reaction of the labelling enzyme to be used. The buffer solution may incorporate therein BSA (bovine serum albumin) as a stabilizer for the enzyme-labelled antibody.

The 2-butanol-containing treating reagent of the present invention does not inhibits the enzymatic reaction. After treatment of the sample, therefore, the treated sample solution can be subjected to the enzyme immunoassay, particularly the homogeneous enzyme immunoassay having no B/F separation process after the immunological reaction. Any immunological method of determination using a process of the immunological reaction between $HbA_{1c}$ and anti-$HbA_{1c}$ antibody can be adopted to the present invention. Examples of the immunological method which can be used for the present invention include the sandwich method using an enzyme label (ELISA), RIA, the latex agglutination method, and homogeneous immunoassay methods such as CEDIA (Cloned Enzyme Donor Immunoassay) and EMIT (Enzyme Multiplied Immuno Test). The treating reagent is most effective in and suitable for the homogeneous enzyme immunoassay which is disclosed in Unexamined Japanese Patent Publication (KOKAI) No. 171460/1985. In this case, the whole blood sample is treated with the treating reagent containing a surfactant and 2-butanol or the whole blood sample is hemolyzed with a surfactant and then treated with a 2-butanol-containing treating reagent. Thereafter, an enzyme-labelled anti-$HbA_{1c}$ antibody is added to the treated sample to cause the antigen-antibody reaction. The $HbA_1c$ concentration or content in the sample can be determined from the decrease in the enzymatic activity.

The immunological determination method according to the invention is not limited to the wet system of analysis as described above. The immunological determination may be carried out in a dry system using a dry analytical element. Examples of such method include the dry method of analysis using a homogeneous enzyme immunoassay as disclosed in Unexamined Japanese Patent Publication (KOKAI) No. 276551/1992 (corresponding to EP-A-0503459). In the dry system of analysis, a liquid sample is applied or spotted on an analytical element so as to effect the immunological binding reaction and the enzymatic reaction within the element. The sample solution is preparatorily treated with 2-butanol present in the treating reagent and then an aliquot of the treated sample solution is applied on the dry analytical element. When the wet method is used for the immunological determination, the 2-butanol added at the step of the treatment will be diluted by the addition of an enzyme-labelled antibody solution. In contrast, the dry system does not include the step of dilution in any of the whole process thereof. Therefore, the concentration of 2-butanol during the course of the enzymatic reaction is substantially the same as that during the course of the 2-butanol treatment. For the purpose of minimizing the adverse effect of 2-butanol on the enzymatic reaction, it is appropriate to lower the 2-butanol concentration to a level in the approximate range of 1 to 2.5% by weight. The promotion of the immunological binding reaction cannot be impaired because the effect of the treatment of $HbA_{1c}$ is substantially saturated at a 2-butanol concentration of 2.5% by weight. When 2-butanol is present at a concentration of about 5.0%, the upper limit of the range of concentration during the course of the treatment mentioned above, the enzymatic activity cannot be halved by the upper limit of the concentration. Therefore, the apparent decrease of the enzymatic activity of the labelling enzyme can be compensated by increasing the amount of the labelling-enzyme.

In an alternative embodiment, only the determination of the activity of the labelling enzyme is carried out by using the dry analytical element. In detail, a dry analysis element having a substrate layer containing the substrate for assay of the labelling enzyme is prepared. The liquid sample is treated with the treating reagent solution of the invention, and then the treated liquid sample is added to a solution containing an enzyme-labelled antibody to take place an antigen-antibody binding reaction. After the completion of the antigen-antibody binding reaction, an aliquot of the reaction mixture is spotted on the dry analytical element to measure the enzymatic activity.

EXAMPLE 1

Preparation of GMB Amylase

Maleimide groups were introduced into α-amylase through the following processing steps. To 1 mL of a 5 mg/mL solution of Bacillus subtilis α-amylase solution (in a 0.1 M glycerophosphate buffer solution, pH 7.0), 100 μl of a 100 mg/mL solution of GMBS (N-(γ-maleimido-butyryloxy)succinimide; produced by DOJIN KAGAKU) in DMF was added and allowed to react at room temperature for 1 hours. The reaction mixture was subjected to the gel filtration through a SEPHADEX G-25 column, which was then eluted with a 0.1 M glycerophosphate buffer solution (pH 7.0). The passing fraction was collected to obtain N-(γ-maleimido-butyryloxy)amidated amylase (GMB amylase). The concentration of thus obtained GMB amylase solution was 1.35 mg/mL. (A) Preparation of Anti-Human $HbA_{1c}$ Monoclonal Antibody A monoclonal antibody IgG against the human $HbA_{1c}$ was prepared through a commonly used process in which immunized cells (spleen cells) obtained by immunizing to mouse were fused with murine myeloma cells, followed by cloning process. In details, 7 μg of natural human hemoglobin $A_{1c}$ dissolved in 1 mM KCN (pH 7.45), 143 μL of RPMI-1640 medium (containing 1 g/L of sodium carbonate, 600 mg/L of L-glutamine and 10 mM of HEPES: pH 6.8) and 200 μL of complete Freund's adjuvant was mixed, and the mixture was administered to a mouse by hypodermic injection as a first priming. The immuno-boosting was carried out every two-weeks. Finally B-lymphocyte was collected from the immunized mouse spleen and fused with murine myeloma cell for cloning. From the resultant clones, the cell line was selected which produced the antibody having specific reactivity to human $HbA_{1c}$ but having substantially no cross-reactivity to other hemoglobin subclasses at all, and thus obtained antibody-forming cells were cultured. By purification of the antibody, the monoclonal antibody specific for human $HbA_{1c}$, anti-human $HbA_{1c}$ IgG, was obtained.

(B) Preparation of Anti-Human $HbA_{1c}$ IgG Fab'

Resultant anti-human $HbA_{1c}$ antibody IgG in an amount of 20 mg was dissolved in 10 mL of a 0.1 M acetate buffer solution (pH 5.5) and then added with 600 μg of activated papain, followed by stirring the mixture at 37° C. for 2 hours. The reaction mixture was then applied to a SUPERDEX-200 gel column, which had been preliminarily equilibrated with a 0.1 M phosphate buffer solution (pH 6.0, containing 1 mM EDTA), followed by elution with the same phosphate buffer solution. The peak fraction of the eluate having the molecular weight of about 100,000 daltons was collected to obtain an anti-human $HbA_{1c}$ IgG F(ab')$_2$. 2 mL of a 0.1 M phosphate buffer solution (pH 6.0) containing 10 mg of the thus prepared anti-human $HbA_{1c}$ IgG F(ab')$_2$ was added with 200 μl of a 10 mg/mL aqueous solution of 2-mercaptoethylamine-HCl salt to proceed the reaction at 37° C. for 90 minutes with stirring. The reaction mixture was subjected to gel filtration by a SEPHADEX G-25, which had been preliminarily equilibrated with a 0.1 M phosphate buffer solution (pH 6.0). The passing fraction was collected to obtain an anti-human $HbA_{1c}$ IgG Fab' (hereinafter referred to as "Fab'").

(C) Preparation of α-Amylase/Fab' Bound 0.1 mg/mL solution of anti-human $HbA_{1c}$ IgG Fab' (referred to simply as "Fab'", hereinafter) in an amount of 6.5 mL prepared by (B) above was added with 2 mg of the GMB amylase prepared by (A) above, and the reaction mixture was maintained at 4° C. overnight to proceed the reaction. The reaction mixture was then applied to a SUPERDEX-200, which had been preliminarily equilibrated with a 20 mM glycerophosphate buffer solution (pH 7.0, containing 10 mM $CaCl_2$). The fraction at the molecular weight of not less than 300,000 was collected to obtain an enzyme-labelled antibody (α-amylase/Fab' bound).

EXAMPLE 2 (Wet System)

Determination of $HbA_{1c}$

Using the enzyme-labelled antibody obtained above, human $HbA_{1c}$ was analyzed by a homogeneous enzyme immunoassay using the following solutions.

Treating Reagent 1 (control; comparative example)

0.1 M MES buffer solution (pH 6.0), 1% BSA (bovine serum albumin), 0.01% sodium azide, and 0.05% Triton X-100.

Treating Reagent 2 (according to the invention)

0.1 M MES buffer solution (pH 6.0), 1% BSA (bovine serum albumin), 0.01% sodium azide, 0.05% Triton X-100, and 5.0% 2-butanol.

Reaction Buffer Solution 50 mM maleic acid (pH 6.5)

Diluting Buffer Solution of α-amylase/Fab' Bound 20 mM glycerophosphate (pH 7.0), 10 mM $CaCl_2$, 0.85% NaCl, and 0.05% sodium azide.

The $HbA_{1c}$ solution (produced by Exocell, 13 mg/mL, PBS) was diluted severally with the treating reagents 1 and 2 to sequentially tripled volumes to prepare a series of solutions having $HbA_{1c}$ concentrations ranging from 0 to 300 pg/mL. About 5 minutes after starting the dilution (meaning that the treatment took about 5 minutes), 50 μL of each of the sequentially diluted solutions was added to a 200-fold diluted solution of the α-amylase/Fab' bound prepared in Example to react each other at 37° C. for 20 minutes. On the other hand, one tablet of Neo Amylase Test "Dai-ichi" (produced by Dai-ichi Pure Chemicals Co., Ltd. containing 45 mg of the blue starch and 3 mg of BSA) was dissolved in 4 mL of the reaction buffer solution to prepare a test solution. 1 mL of the test solution was added to each of the reaction solution to proceed enzymatic reaction at 37° C. for one hour. The reaction was terminated by addition of 0.5 mL of 0.5 N $NaCO_3$ buffer solution. After agitating, the solution was subjected to centrifugation at 3,000 rpm for 5 minutes, and the supernatant was taken out. The supernatant was subjected to light absorption analysis at 620 nm to determine the quantity of blue dyestuff which had been solubilized by the enzymatic reaction and dissolved in the supernatant. FIG. 1 shows the interrelation between the absorbance observed and the concentration of human $HbA_{1c}$.

As compared with the treating reagent 1 containing no 2-butanol (control, indicated by the mark —■— in the diagram), the treating reagent 2 containing 2-butanol (treating reagent according to the invention, indicated by the mark —Δ— in the diagram) showed a large decline of the activity of the labelling enzyme in consequence of the addition of $HbA_{1c}$ subjected to the test. Based on the amount of the $HbA_{1c}$ required for halving the absorbance from the original magnitude, about 1.0, prior to the addition of the $HbA_{1c}$, the treating reagent of the invention was found to increase the sensitivity to about 20 times the original value. A larger change of absorbance was observed with respect to variation of the $HbA_{1c}$. It was confirmed that the treating reagent of the invention allowed the determination of $HbA_{1c}$ to be attained at a higher S/N ratio, namely, with higher sensitivity. As noted from the absorbance prior to the addition of the $HbA_{1c}$, the 2-butanol used in the invention brought about no effect on the enzymatic activity of the labelling enzyme.

EXAMPLE 3

Figure 2:
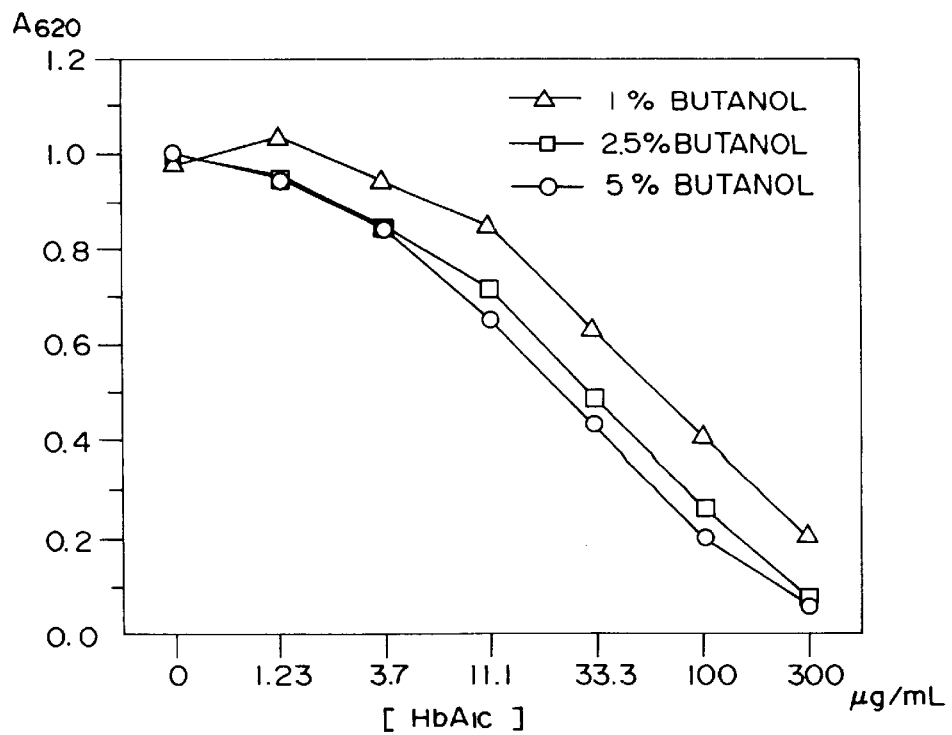
FIG. 2 is a diagram showing the effects of the treatment using 2-butanol at varying concentrations on the homogeneous enzyme immunoassay.

An enzyme immunoassay was carried out by faithfully following the procedure of Example 2 while changing the 2-butanol concentration in the treating reagent 2 to 1% and 2.5%. As shown in FIG. 2, the sensitivity rose in accordance with the 2-butanol concentration increased. The data indicate that 2-butanol used at concentrations in the range of 1 to 2.5% was fully effective in enhancing the sensitivity.

EXAMPLE 4

Preparation of Dry Analysis Element for $HbA_{1c}$ Determination

On a colorless and transparent polyethylene terephthalate (PET) sheet (support) coated with a gelatin undercoating and having a thickness of 180 μm, coated was a reagent solution containing a cross-linking reagent, followed by drying, to form a reagent layer so that respective components had the coverages as set forth below.

| | |
|---|---|
| Alkaline-treated Gelatin | 14.5 g/m² |
| Nonylphenoxy polyethoxyethanol | 0.2 g/m² |
| (Containing 9 to 10 (average) of Oxyethylene Units) | |
| Glucose Oxidase | 5,000 IU/m² |
| Peroxidase | 15,000 IU/m² |
| Glucoamylase | 5,000 IU/m² |
| 2-(4-hydroxy-3,5-dimethoxyphenyl)-4-[4-(dimethylamino)phenyl]-5-phenetyl-imidazole (Leuco Dye) Acetate | 0.38 g/m² |
| Bis[(vinylsulfonylmethylcarbonyl)amino]-methane | 0.1 g/m² |

On the reagent layer, an aqueous solution of an adhesive agent was coated to have the following coverage, and then dried to form an adhesive layer.

| | |
|---|---|
| Alkaline-treated Gelatin | 14.5 g/m² |
| Nonylphenoxy polyethoxyethanol | 0.2 g/m² |
| (Containing 9 to 10 (average) of Oxyethylene Units) | |

Then, an aqueous solution containing the following reagent was coated over the surface of the adhesive layer to have the following coverages to swell the gelatin layer and a tricot knitted cloth made by knitting PET spun yarn of 36 gage corresponding to 50 deniers and having a thickness of about 250 μm was laminated thereon, by pressing with a uniform light pressure to form a porous spreading layer.

| | |
|---|---|
| Nonylphenoxy polyethoxyethanol | 0.2 g/m² |
| (Containing 9 to 10 (average) of Oxyethylene Units) | |
| Bis[(vinylsulfonylmethylcarbonyl)amino]-methane | 0.1 g/m² |

Subsequently, on the spreading layer, an aqueous solution of a substrate was coated, followed by drying, to have the following coverages, whereby the porous spreading layer (knit fabric layer) had a function of a substrate layer. Thus, a multi-layered analytical element for the quantitative analysis of $HbA_{1c}$ was prepared.

| | |
|---|---|
| MEGAFAC F142D | 0.1 g/m² |
| (fluorine surfactant produced by DAI NIPPON INK & CHEMICALS INC.) | |
| (containing an average of 10 Oxyethylene Units) | |
| Carboxymethylated starch | 5 g/m² |
| Mannitol | 2 g/m² |
| Amylase inhibitor | 1 million U/m² |
| (produced by FUJIREBIO INC. and marketed under product code of "1–1001C"; JP-A-61-74587) | |

The thus prepared element was cut into tips each having 15 mm square, and each tip was placed in a slide frame described in Unexamined Japanese Patent Publication (KOKAI) No. 63452/1982 to prepare a analysis slide for the quantitative determination of $HbA_{1c}$. In the meantime, the amylase inhibitor "1-1001C" used herein was an inhibitor intended to act on similar species of amylase possibly contained in a sample and was incapable of inhibiting the enzymatic activity of the *Bacillus subtilis* α-amylase used as the labelling enzyme (Unexamined Japanese Patent Publication (KOKAI) No. 122112/1993).

The $HbA_{1c}$ solution (produced by Exocell, 13 mg/mL, PBS) was diluted severally with the treating reagents 1 and 2 to sequentially doubled volumes to prepare a series of solutions having $HbA_{1c}$ concentrations ranging from 7.5 to 240 mg/mL. The treating reagent 1 and the treating reagent 2 were used in their unmodified form each as a solution containing $HbA_{1c}$ at a concentration of 0 mg/dL. About 5 minutes after starting the dilution (meaning that the treatment took about 5 minutes), 50 μL of each of the sequential diluted solutions was added to 30-fold diluted solution of the α-amylase/Fab' bound prepared in Example 1 to react each other at 37° C. for 20 minutes. Subsequently, 10 μL of each of the reaction solutions was spotted on the aforementioned $HbA_{1c}$ analytical slide which was maintained at 37° C., and the optical density of the reflected light at 650 nm was measured from the PET support side. The difference in optical density ($\Delta OD_{6-4}$) of the reflected lights measured respectively after the lapse of 4 minutes and 6 minutes was determined. A calibration curve was prepared based on the result of determination. The calibration curve thus prepared is shown in FIG. 3.

Figure 3:
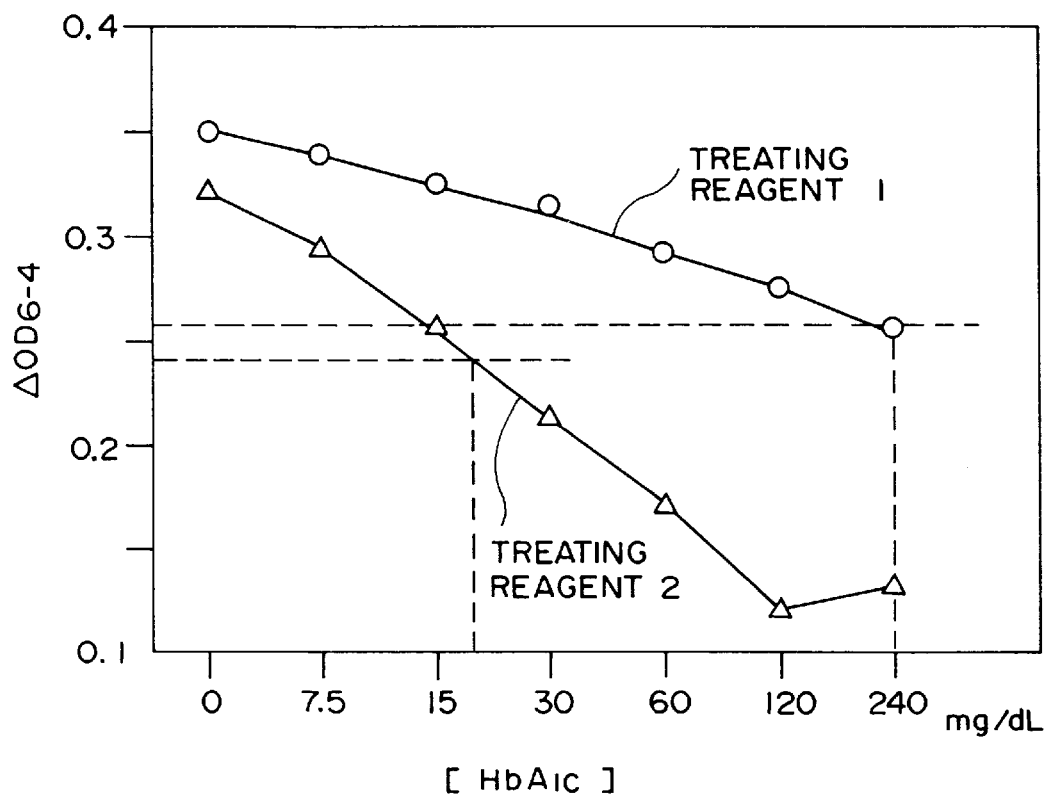
FIG. 3 is a diagram showing a calibration curve used in the method of determination in Example 4 of the present invention.

As compared with the treating reagent 1 containing no 2-butanol (control, indicated by the mark —Δ— in the FIG. 3), the treating reagent 2 containing 2-butanol (treating reagent according to the invention, indicated by the mark —○— in the FIG. 3) showed a large decline of the activity of the labelling enzyme in consequence of the addition of $HbA_{1c}$ subjected to the test. For the sake of the quantitative evaluation of the ratio of sensitivity, the amounts of HbAic required for lowering the absorbance from the original magnitudes, about 0.35 (treating agent 1 for control) and about 0.32 (treating reagent 2 according to the invention) prior to the addition of $HbA_{1c}$, severally to about ¼, namely the amounts of $HbA_{1c}$ required for lowering the original magnitudes of absorbance to about ¾ (about 0.16 in the treating reagent 1 for control and about 0.24 in the treating reagent 2 for this invention), were used as criteria of sensitivity by way of approximate alternative evaluation of the amounts of $HbA_{1c}$ required for halving the absorbance. As noted from the amounts of $HbA_{1c}$ indicated by a dotted line in FIG. 3, the treating reagent of the present invention was found to produce a notable rise of sensitivity ranging from at least about 12 times to about 20 times the original magnitude. A larger change of absorbance was observed with respect to variation of the $HbA_{1c}$. It was confirmed that the treating reagent of this invention permitted the determination of $HbA_{1c}$ to be attained at a higher S/N ratio, namely, with higher sensitivity.

As has been described hereinbefore, according to the present invention, a sample containing a hemoglobin derivative such as hemoglobin Aic is mixed and treated with 2-butanol-containing treating reagent. As an advantageous result, the immunoassay can be attained not only with high sensitivity of detection but also at a high S/N ratio. Even when an enzyme is used as a label for an antibody or an antigen in the assay, the present treating reagent will not affect or suppress the enzymatic activity of the labelling enzyme. Accordingly, the method of the present invention can be adopted to the various enzyme immunoassays including a homogeneous enzyme immunoassay. It allows a sample to be analyzed quickly by a simple procedure at high sensitivity for the determination of the hemoglobin derivative such as hemoglobin $A_{1c}$.

What is claimed is:

1. A method for immunological determination of a hemoglobin derivative; comprising treating a sample solution containing said hemoglobin derivative with a treating reagent containing 2-butanol and a hemolysis agent, and immunologically analyzing the treated sample solution to determine the quantity of the hemoglobin derivative in the sample solution.

2. The method according to claim 1, wherein said immunological determination is effected by enzyme immunological analysis.

3. The method according to claim 2, wherein an enzyme-labelled antibody against said hemoglobin derivative is added to said treated sample solution so that an antigen-antibody reaction takes place, and wherein an aliquot of the reaction solution after the completion of the antigen-antibody reaction is applied on a dry analytical element to determine the enzymatic activity of the enzyme label, thereby to determine the quantity of said hemoglobin derivative contained in said sample solution.

4. The method according to claim 2, wherein an aliquot of said treated sample solution is applied to a dry analytical element so that an antigen-antibody reaction between said hemoglobin derivative and an enzyme-labelled antibody against the hemoglobin derivative takes place and an enzymatic reaction of the enzyme label takes place within said element.

5. The method according to claim 1, wherein said sample solution is a whole blood sample.

6. The method according to claim 1, wherein said treating reagent contains 2-butanol in an amount such that the final concentration thereof at the treatment may be in the approximate range of 1.0 to 5.0% by weight.

7. The method according to claim 1, wherein said hemoglobin derivative is glycated hemoglobin.

8. The method according to claim 7, wherein said glycated hemoglobin is glycosylated hemoglobin ($HbA_{1c}$).

9. The method according to claim 1, wherein said hemolysis agent is a nonionic surfactant.

* * * * *